United States Patent
Cho et al.

(10) Patent No.: US 7,311,860 B2
(45) Date of Patent: Dec. 25, 2007

(54) 1,3,5-TRICYANO-2,4,6-TRIS(VINYL)BENZENE DERIVATIVES AND METHOD FOR PREPARING THE SAME

(75) Inventors: Bong-Rae Cho, Seoul (KR); Seung-Joon Jeon, Seoul (KR); Min-Haeng Cho, Seoul (KR)

(73) Assignee: Korea University Foundation, Seoul (KR)

( * ) Notice: Subject to any disclaimer, the term of this patent is extended or adjusted under 35 U.S.C. 154(b) by 557 days.

(21) Appl. No.: 10/484,704

(22) PCT Filed: Feb. 28, 2002

(86) PCT No.: PCT/KR02/00349

§ 371 (c)(1),
(2), (4) Date: Jan. 26, 2004

(87) PCT Pub. No.: WO03/011817

PCT Pub. Date: Feb. 13, 2003

(65) Prior Publication Data

US 2004/0251452 A1    Dec. 16, 2004

(30) Foreign Application Priority Data

Jul. 27, 2001  (KR) ................ 2001-45504

(51) Int. Cl.
*G02B 5/02*   (2006.01)
*G02C 7/10*   (2006.01)
*G03B 11/00*  (2006.01)
*C07C 255/58* (2006.01)

(52) U.S. Cl. ...................... 252/582; 558/419

(58) Field of Classification Search ............... 558/419; 252/582

See application file for complete search history.

(56) References Cited

OTHER PUBLICATIONS

Cho et al. "1,3,5-Tricyano-2,4,6-tris(vinyl)benzene Derivatives with Large Second-Order Nonlinear Optical Properties" Journal of the American Chemical Society, 2001, vol. 123, pp. 6421-6422.*
Cho, B.R. et al. "1,3,5-Tricyano-2,4,6-tris(vinyl)benzene Derivatives with Large Second-Order Nonlinear Optical Properties", J.Am.Chem.Soc., Am. Chem. Soc., vol. 123 pp. 6421-6422, (2001).
Cho, B.R. et al. "Two Photon Absorption Properties of 1,3,5-Tricyano-2,4,6-tris(styryl)benzene Derivatives", *J. Am. Chem. Soc.*, Am. Chem. Soc., vol. 123 pp. 10039-10045, (2001).

* cited by examiner

*Primary Examiner*—Rebecca Anderson
*Assistant Examiner*—Joseph R. Kosack
(74) *Attorney, Agent, or Firm*—Birch, Stewart, Kolasch & Birch, LLP

(57) ABSTRACT

The present invention relates to 1,3,5-tricyano-2,4,6-tris(vinyl)benzene derivatives and method for preparing the same. The 1,3,5-tricyano-2,4,6-tris(vinyl)benzene derivatives can be prepared by refluxing 1,3,5-tricyanomesitylene with N-formylamine dimethylacetal or substituted benzaldehyde, or by the Wittig reaction of 1,3,5-tricyano-2,4,6-tris[(diethoxyphosphoryl)methyl]benzene with substituted benzaldehyde. The 1,3,5-tricyano-2,4,6-tris(vinyl)benzene derivatives exhibit large first hyperpolarizability in solution and significant second harmonic generation (SHG) in the powder state, and are useful as optical devices such as electro-optic modulators, optical switch, or the like for treating optical signal in optical communication industry.

2 Claims, 2 Drawing Sheets

# 1,3,5-TRICYANO-2,4,6-TRIS(VINYL)BENZENE DERIVATIVES AND METHOD FOR PREPARING THE SAME This application is the U.S. National Phase entry under §371 of International Application No. PCT/KR02/00349, filed Feb. 28, 2002, the entire contents of which are hereby incorporated by reference and for which priority is claimed under 35 U.S.C. § 120. This application also claims priority of Application No. 2001-45504 filed in Korea on Jul. 27, 2001, the entire contents of which are hereby incorporated by reference and for which priority is claimed under 35 U.S.C. §119.

TECHNICAL FIELD

The present invention relates to 1,3,5-tricyano-2,4,6-tris (vinyl)benzene derivatives and method for preparing the same, more particularly, the present invention relates to 1,3,5-tricyano-2,4,6-tris(vinyl)benzene derivatives 1~3 and method for preparing the same, wherein the derivatives are synthesized either by refluxing 1,3,5-tricyanomesitylene with N-formylamine dimethylacetal or substituted benzaldehyde, or by the Wittig reaction of 1,3,5-tricyano-2,4,6-tris [(diethylphosphoryl)methyl]benzene with substituted benzaldehyde.

PRIOR ART

The nonlinear optical materials are the core materials used in electro-optic modulators, optical switch, optical recording, optical communication and so on because they change the properties of light such as frequency, phase, amplitude by interacting with the electric field. The organic nonlinear optical materials used in this field at the present time are dipolar molecules having electron donor and acceptor at the ends of the conjugated double bond. The macroscopically nonlinear optical property was obtained by applying a high electric field on the thin film made from these molecules (electric poling).

The two-photon dyes are materials getting to the excited state by absorbing two photon spontaneously and are applicable to three-dimensional optical storage, two-photon fluorescence excitation microscopy, two-photon optical power limiting, two-photon upconverted lasing, photodynamic therapy and so on. The most popular dye of the present time is a quadrupolar molecule having an electron donor or an electron acceptor at the ends of the conjugated double bond.

As a prior reference, the Korean Patent No. 169581 discloses an organic nonlinear optical material which is composed of an azo compound having diazonium cation as a functional group receiving an electron and dialkylamino group as a functional group donating an electron. The Korean Patent No. 169910 discloses nonlinear optical polyimide, a method for preparing the same and an optical waveguide-type photoelectric element using the above nonlinear optical polyimide.

In order to use the organic nonlinear optical materials as a material of the information and communication, it is required to have a large nonlinear optical property and high thermal stability in the solid state [*J. Mater. Chem.*, 1999, 9, 1905]. Most of the nonlinear optical materials, which are in use at the present time, are dipolar molecules having the donor and the acceptor at the ends of the conjugated double bond. These materials can be used by obtaining macroscopic nonlinear optical property through electric poling process [*Science*, 2000, 288, 119]. This process is an arranging the dipolar molecules in the thin layer in the direction of one side by applying a high voltage after heating the thin layer over the Tg. But, this process has many technical problems. In addition, there is a problem that the dipolar molecules in the thin layer have a tendency to relax in the opposite direction which is more stable thermodynamically so that the nonlinear optical property is reduced with time. As another type of the nonlinear optical materials studied in the present time, there is an octupolar molecule [*Chem. Mater.*, 2001, 13, 9205, *J. Am. Chem. Soc.*, 1998, 120, 2563, *Nature*, 1995, 374, 339, *Chem. Rev.*, 1994, 94, 77, *Nonlinear Optics*, 1991, 1, 3]. This molecule has a pretty large nonlinear optical property while not having dipole moment. However, the octupolar molecule, which has macroscopic nonlinear optical property as much as being practical in the solid state, had not yet been found. The two-photon dyes are materials getting to the excited state by absorbing two photon at the same time and the dyes are useful for a variety of applications such as three-dimensional optical storage [*Science*, 1989, 245, 843, *Opt. Commun.* 1995, 119, 341, *Nature*, 1999, 398, 51], two-photon fluorescence excitation microscopy [*Science*, 1990, 248, 73, *Opt. Lett.*, 1995, 20, 2532, *Neuron*, 1997, 18, 351, *Science*, 1997, 276, 2039, *Proc. Natl. Acad. Sci. USA* 1996, 93, 10763, *Proc. Natl. Acad. Sci. USA* 1994, 91, 6629], two-photon optical power limiting [*SPIE Proc.* 1998, 3472, 91, *Appl. Phys. Lett.* 1995, 67, 2433, *Opt. Lett.* 1997, 22, 1843], two-photon upconverted lasing [*Rep. Prog. Phys.* 1996, 59, 1041, *Appl. Phys. Lett.* 1995, 67, 3703, *Chem. Mater.* 1995, 7, 1979], photodynamic therapy [*J. Clin. Laser, Med. Surg.* 1997, 15, 201] and so on. In the present time, the quadrupolar molecule is in use most generally, wherein the quadrupolar molecule has an electron donor or acceptor at the ends of the conjugated double bond. If this molecule has the second-order nonlinear optical property, the applicability of this molecule will be more widely. However, this molecule does not have second-order nonlinear optical property because its symmetrical structure.

Accordingly, it is an object of the present invention to provide an organic nonlinear optical material having a large nonlinear optical property.

It is another object of the present invention to provide an organic nonlinear optical material having a macroscopically nonlinear optical property in the solid state.

It is a further object of the present invention to provide an organic nonlinear optical material which has a large second-order nonlinear optical property and a large two-photon absorption efficiency.

DISCLOSURE OF THE INVENTION

To achieved the object, the present inventors synthesized 1,3,5-tricyano-2,4,6-tris(vinyl)benzene derivatives 1~3 either by refluxing 1,3,5-tricyanomesitylene with N-formylamine dimethylacetal or substituted benzaldehyde, or by the Wittig reaction of 1,3,5-tricyano-2,4,6-tris[(diethylphosphoryl)methyl]benzene with substituted benzaldehyde.

BRIEF DESCRIPTION OF THE DRAWINGS

The above objects, features and advantages of the present invention will become more apparent from the following detailed description when taken in conjunction with the accompanying drawings, in which.

DETAILED DESCRIPTION OF THE PREFERRED EMBODIMENT

Figure 1:
FIG. 1 is a graph showing the intensity of HRS signal according to the concentration of 1,3,5-tricyano-2,4,6-tris (p-piperidylstyryl)benzene, the preferred embodiment of the present invention.

The present invention relates to 1,3,5-tricyano-2,4,6-tris(vinyl)benzene derivatives and method for preparing the same.

1,3,5-tricyano-2,4,6-tris(vinyl)benzene derivatives according to the present invention are represented by the following chemical formula I and II:

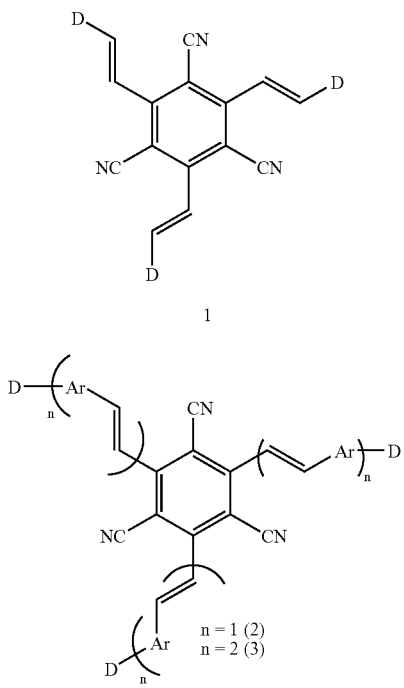

wherein, D is $NR_1R_2$ or $X_1R_3$;
wherein $R_1$, $R_2$ and $R_3$ are independently hydrogen, alkyl, hydroxyalkyl, alkyl moiety, phenyl or aryl moiety, and
$X_1$ is oxygen or sulfur; and
Ar is an aromatic group represented by the following chemical formula III and n is an integer of 0 to 3;

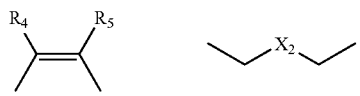

wherein, $R_4$, $R_5$, $R_6$, $R_7$, $R_8$ and $R_9$ are independently hydrogen, halogen, aryl, hydroxy, alkoxy, aryloxy, alkyl, CN, alkyl moiety, phenyl or aryl moiety, and
$X_2$ is oxygen, sulfur or $NR_{10}$
wherein $R_{10}$ is hydrogen, alkyl, hydroxyalkyl, alkyl moiety, phenyl, aryl moiety, halogen, hydroxy, alkoxy, aryloxy or CN.

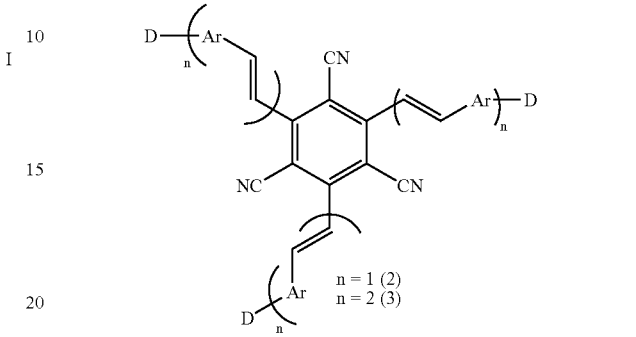

wherein, D is $NR_1R_2$ or $X_1R_3$;
wherein $R_1$, $R_2$ and $R_3$ are independently hydrogen, alkyl, hydroxyalkyl, alkyl moiety, phenyl or aryl moiety, and
$X_1$ is oxygen or sulfur; and
Ar is an aromatic group represented by the following chemical formula III and n is an integer of 0 to 3;

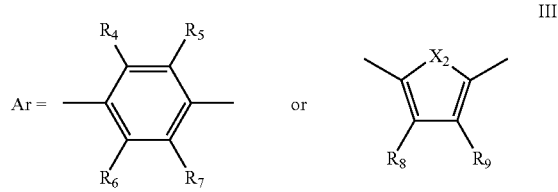

wherein, $R_4$, $R_5$, $R_6$, $R_7$, $R_8$ and $R_9$ are independently hydrogen, halogen, aryl, hydroxy, alkoxy, aryloxy, alkyl, CN, alkyl moiety, phenyl or aryl moiety, and
$X_2$ is oxygen, sulfur or $NR_{10}$
wherein $R_{10}$ is hydrogen, alkyl, hydroxyalkyl, alkyl moiety, phenyl, aryl moiety, halogen, hydroxy, alkoxy, aryloxy or CN.

1,3,5-tricyano-2,4,6-tris(vinyl)benzene derivatives 1~3 of the present invention represented by the above formulas I and II are synthesized either by refluxing 1,3,5-tricyanomesitylene with N-formylamine dimethylacetal or substituted benzaldehyde, or by the Wittig reaction of 1,3,5-tricyano-2,4,6-tris[(diethylphosphoryl)methyl]benzene with substituted benzaldehyde. The method of synthesis of the derivatives is shown below.

Scheme 1

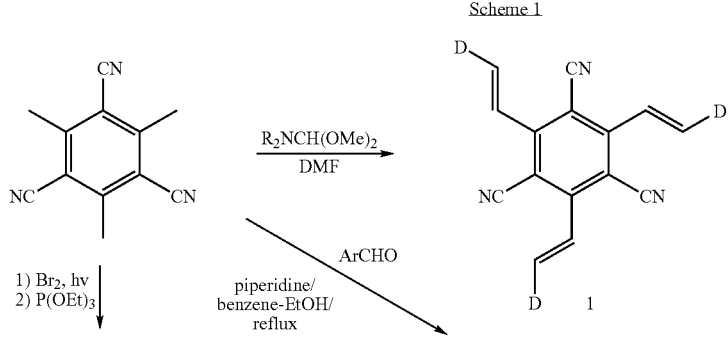

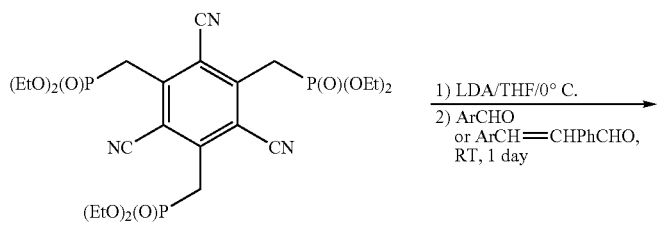 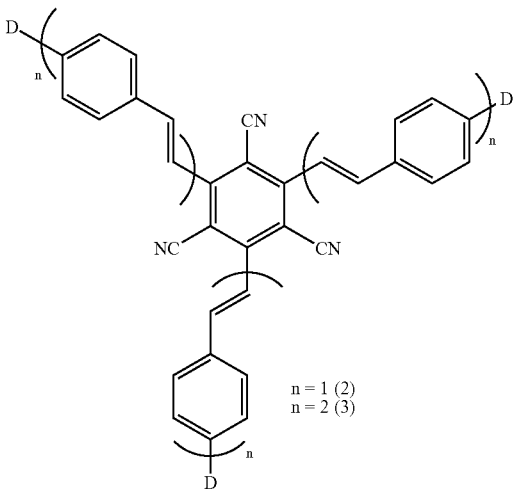

Now, specific embodiments of the present invention will now be described by the following examples. However, it should be understood that the scope of the present invention is not limited thereto.

EXAMPLES

The present inventor noticed that if octupolar compounds containing three stilbene structure in one molecule are synthesized, the octupolar compounds has excellent nonlinear optical property and macroscopically nonlinear optical and has a large two-photon absorption efficiency so that the compounds has a large applicability in the field of electro-optic devices, extremely-highly integrated optical memory storage, two-photon spectrofluorimeter, two-photon optical power limiting and etc. Accordingly, the present inventor synthesized 1,3,5-tricyano-2,4,6-tris(vinyl)benzene derivatives 1~3 represented by the above formula I and II, and measured nonlinear optical property and two-photon absorption cross sections of the above derivatives. In the following examples, the number of the compound is as shown in Chart 1.

Chart 1

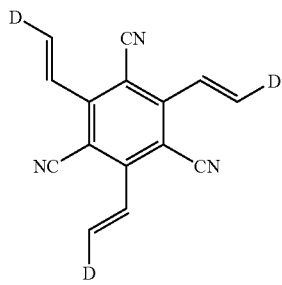

1

D = H (a), Me (b), OH (c), OMe (d), NH$_2$ (e),
NMe$_2$ (f), NEt$_2$ (g), NBu$_2$ (h), piperidyl (i), NPh$_2$ (j)

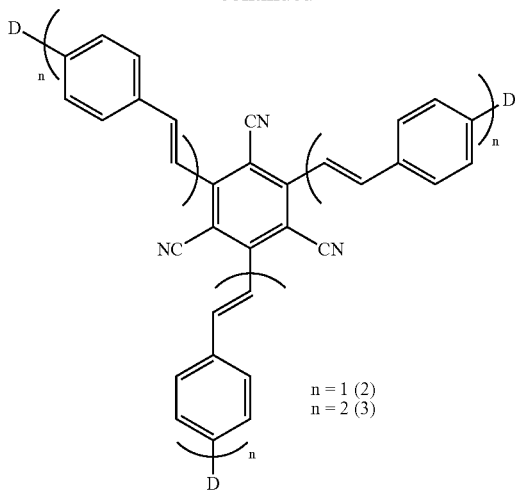

Example 1

Synthesis of 1,3,5-tricyano-2,4,6-tris(2-dialkylaminovinyl)benzene

A solution of 1,3,5-tricyanomesitylene (0.50 g, 2.6 mmol) and N,N-dimethylformamide diethylacetal (1.0 g, 8.5 mmol) in 2 mL of DMF was refluxed for 12 hrs. The product was filtered, washed with ether, and recrystallized in MeOH-CH$_2$Cl$_2$. Compound 1b was prepared by the same procedure except that dimethylacetal of N-formylpiperidine was used. The yield (%), melting point (° C.), IR (KBr, cm$^{-1}$), $^1$H NMR (300 MHz, CDCl$_3$), CMR (75 MHz, CDCl$_3$), and combustion analysis data for 1a-b are as follows. Chemical shifts are in ppm and J values in Hz.

(i) 1,3,5-Tricyano-2,4,6-tris(2-dimethylaminovinyl)benzene (1f)

Yield 92%; mp 252° C. subl; IR 2192 (CN), 1610 (C=C); $^1$H NMR δ 7.73 (d, 3H, J=13.2), 5.30 (d, 3H, J=13.2), 2.99 (s, 18H). CMR δ 150.9, 148.5, 120.3, 95.4, 91.6, 40.8. Anal. Calcd for C$_{21}$H$_{24}$N$_6$: C, 69.97; H, 6.71; N, 23.32. Found: C, 69.95; H, 6.69; N, 23.25.

(ii) 1,3,5-Tricyano-2,4,6-tris(2-piperidin-1-ylvinyl)benzene (1i)

Yield 60%; mp 190° C. subl; IR 2190 (CN), 1600 (C=C); $^1$H NMR δ 7.63 (d, 3H, J=13.2), 5.47 (d, 3H, J=13.2), 3.29 (m, 12H), 1.65 (m, 18H). CMR δ 151.3, 148.0, 120.3, 95.5, 91.6, 49.8, 25.5, 24.2. Anal. Calcd for $C_{30}H_{36}N_6$: C, 74.97; H, 7.55; N, 17.48. Found: C, 74.96; H, 7.58; N, 17.49.

Example 2

Synthesis of 1,3,5-tricyano-2,4,6tris(styryl)benzene and 1,3,5-tricyano-2,4,6tris[4-(aminostyryl)]benzene (1) Synthesis of 1,3,5-Tricyano-2,4,6-tris(bromomethyl) benzene A solution of 1,3,5-tricyanomesitylene (6.0 g, 31 mmol) and $Br_2$ (17.2 g, 108 mmol) in 250 mL of $CCl_4$ was irradiated with 400 W tungsten lamp for 2 hrs. After removing the excess $Br_2$ with $Na_2S_2O_3$ (aq), the product was extracted with $CH_2Cl_2$, and purified by column chromatography with hexane/ethyl acetate (10/1) to obtain 1,3,5-tricyano-2,4,6-tris(bromomethyl)benzene as white solid. Yield, 12.6 g (95%); mp 120° C.; IR 2229 (CN); $^1$H NMR δ 4.80 (s, 6H).

(2) Synthesis of 1,3,5-Tricyano-2,4,6-tris[(diethoxyphosphoryl)methyl]benzene

A solution of 1,3,5-tricyano-2,4,6-tris(bromomethyl)benzene (1.0 g, 2.3 mmol) and $P(OEt)_3$ (1.6 g, 14 mmol) in 60 mL of toluene was refluxed for 4 hrs. The solvent was removed in vacuo and the product was purified by column chromatography with hexane/ethyl acetate (10/1) as the eluent to obtain colorless oil. Yield, 0.97 g (69%); IR 2299 (CN), 1263 (P=O); $^1$H NMR δ 4.21 (q, 12H, J=7.2), 3.73 (d, 6H, J=22.1) 1.32 (t, 18H, J=7.2).

(3) Synthesis of 1,3,5-tricyano-2,4,6-tris(styryl)benzene and 1,3,5-tricyano-2,4,6-tris[4-(aminostyryl)]benzene LDA (1.5 M, 1.0 mL) was slowly added to a stirred solution of 1,3,5-tricyano-2,4,6-tris[(diethoxyphosphoryl)methyl]benzene (0.19 g, 31 mmol) in 10 mL of THF at 0° C. The mixture was stirred for 30 minutes. Into the above solution, substituted benzaldehyde or 4-(p-aminostyryl)benzaldehyde (124 mmol) in 5.0 mL of THF was added slowly and stirred for 1 day. The solvent was evaporated and the product was purified by column chromatography with hexane/ethyl acetate (3/1) as the eluent. The yield (%), melting point (° C.), IR (KBr, cm$^{-1}$), $^1$H NMR (300 MHz, CDCl$_3$), CMR (75 MHz, CDCl$_3$), and combustion analysis data for 1a-b are as follows. Chemical shifts are in ppm and J values in Hz.

(i) 1,3,5-Tricyano-2,4,6-tris(p-methoxystyryl)benzene (2d)

Yield 68%; mp 182-184° C.; IR 2220 (CN), 1565 (C=C); $^1$H NMR δ 7.74 (d, 3H, J=16.5), 7.61 (d, 6H, J=8.6), 7.31 (d, 3H, J=16.5), 6.96 (d, 6H, J=8.6), 3.87 (s, 9H). CMR δ 161.3, 149.0, 141.8, 129.5, 127.7, 118.5, 115.9, 114.4, 107.7, 55.5. Anal. Calcd for $C_{36}H_{27}N_3O_3$: C, 78.67; H, 4.95; N, 7.65. Found: C, 78.38; H, 5.10; N, 7.55.

(ii) 1,3,5-Tricyano-2,4,6-tris(p-diethylaminostyryl)benzene (2g)

Yield 76%; mp 270-272° C.; IR 2214 (CN), 1595 (C=C); $^1$H NMR δ 7.75 (d, 3H, J=16.2), 7.52 (d, 6H, J=8.8), 7.20 (d, 3H, J=16.2), 6.67 (d, 6H, J=8.8), 3.42 (q, 12H, J=7.2), 1.21 (t, 18H, J=7.2). CMR δ 149.4, 149.1, 142.0, 129.8, 122.4, 116.8, 115.6, 111.3, 105.4, 44.6, 12.7. Anal. Calcd for $C_{45}H_{48}N_6$: C, 80.32; H, 7.19; N, 12.49. Found: C, 80.30; H, 7.22; N, 12.43.

(iii) 1,3,5-Tricyano-2,4,6-tris(p-piperidinylstyryl)benzene (2i)

Yield 83%; mp 204-205° C.; IR 2208 (CN), 1596 (C=C); $^1$H NMR δ 7.74 (d, 3H, J=16.2), 7.54 (d, 6H, J=8.6), 7.25 (d, 3H, J=16.2), 6.91 (d, 6H, J=8.6), 3.31 (m, 12H), 1.67 (m, 18H). CMR δ 152.8, 149.2, 141.8, 129.3, 124.8, 117.0, 116.5, 114.9, 106.3, 49.2, 25.5, 24.4. Anal. Calcd for $C_{48}H_{48}N_6$: C, 81.32; H, 6.82; N, 11.85. Found: C, 81.40; H, 6.82; N, 11.83.

(iv) 1,3,5-Tricyano-2,4,6-tris(p-diphenylaminostyryl)benzene (2j)

Yield, 86%; mp 290° C.; IR 2224 (CN), 1588 (C=C); $^1$H NMR δ 7.73 (d, 3H, J=15.9), 7.50 (d, 6H, J=8.7), 7.32 (d, 3H, J=15.9), 7.30-7.25 (m, 12H), 7.15-7.03 (m, 24H). CMR δ 149.7, 149.0, 146.7, 141.6, 129.3. 128.9, 128.1, 125.2, 123.9, 121.8, 118.4, 116.0, 107.3. Anal. Calcd for $C_{69}H_{48}N_6$: C, 86.2; H, 5.03; N, 8.74. Found: C, 86.0; H, 5.11; N, 8.89.

(v) 1,3,5-Tricyano-2,4,6-tris[4-(p-dibutylaminostyryl)styryl]benzene (3h)

Yield 73%; mp 70-72° C.; IR 2216 (CN), 1650, 1522 (C=C); $^1$H NMR δ 7.81 (d, 3H, J=16.5), 7.62 (d, 6H, J=8.4), 7.53 (d, 6H, J=8.4), 7.44 (d, 3H, J=16.5), 3.26 (t, 6H, J=8.7), 7.15 (d, 3H, J=15.9), 6.91 (d, 3H, J=15.9), 6.64 (d, 6H, J=8.7), 3.26 (t, 12H, J=6.9), 1.61-1.33 (m, 24H), 0.99 (t, 18H, J=6.9). CMR δ 148.7, 148.0, 141.9, 140.6, 132.9, 130.4, 128.2, 128.0, 126.2, 123.9, 122.5, 119.7, 115.8, 111.5, 107.9, 50.8, 29.5, 20.4, 14.1. Anal. Calcd for $C_{81}H_{90}N_6$: C, 84.77; H, 7.90; N, 7.32. Found: C, 84.58; H, 8.05; N, 7.37.

(vi) 1,3,5-Tricyano-2,4,6-tris[4-(p-piperidinylstyryl)styryl]benzene (3i)

Yield 61%; mp >300° C.; IR 2215 (CN), 1650, 1522 (C=C); $^1$H NMR δ 7.81 (d, 3H, J=15.9), 7.64 (d, 6H, J=8.4), 7.55 (d, 6H, J=8.4), 7.45 (d, 3H, J=15.9), 7.42 (d, 6H, J=8.6), 7.16 (d, 3H, J=15.9), 6.98 (d, 3H, J=15.9), 6.93 (d, 6H, J=8.6), 3.25 (m, 12H), 1.71 (m, 18H). CMR δ 151.5, 148.6, 141.8, 140.2, 133.2, 130.1, 128.5, 128.2, 127.6, 127.3, 126.5, 124.2, 119.7, 115.7, 107.9, 49.9, 25.7, 24.4. Anal. Calcd for $C_{72}H_{66}N_6$: C, 85.17; H, 6.55; N, 8.28. Found: C, 85.25; H, 6.51; N, 8.25.

(vii) 1,3,5-Tricyano-2,4,6-tris[4-(p-diphenylaminostyryl)styryl]benzene (3j)

Yield 54%; mp 126° C.; IR 2215 (CN), 1580, 1483 (C=C); $^1$H NMR δ 7.82 (d, 3H, J=16.5), 7.66 (d, 6H, J=8.7), 7.57 (d, 6H, J=8.7), 7.47 (d, 3H, J=16.5), 7.42 (d, 6H, J=8.7), 7.30-7.27 (m, 9H), 7.18 (d, 3H, J=15.0), 7.13-7.04 (m, 27H), 7.02 (d, 3H, J=15.0). CMR δ 154.4, 148.6, 147.6, 147.2, 143.5, 141.9, 139.8, 133.6, 130.7, 129.6, 129.2, 128.2, 127.5, 126.7, 125.8, 124.5, 124.0, 123.1, 120.1. Anal. Calcd for $C_{93}H_{66}N_6$: C, 88.12; H, 5.25; N, 6.63. Found: C, 88.39; H, 5.26; N, 6.35.

Example 3

Nonlinear Optical Property(β) and Thermal Stability of 1,3,5-tricyano-2,4,6-tris(vinyl)benzene derivatives The β values of the 1,3,5-tricyano-2,4,6-tris(vinyl)benzene derivatives 1-3 were measured at 1560 nm by Hyper-Rayleigh Scattering (HRS) method (*Acc. Chem. Res.* 1998, 103, 4992). The intensity of second-harmonic radiation, which is generated when the solution of nonlinear optical materials in CHCl$_3$ is irritated, is described by the following expression.

$$I_{2\omega}(\text{solution}) = K(N_s <\beta_s^2> + N_c <\beta_c^2>)I_\omega^2 \quad (1)$$

wherein, $N_s$ and $N_c$ represent the concentration of solvent and chromophore, respectively; $<\beta^2>$ is the orientational average of the first hyperpolarizability; $I_\omega$ and $I_{2\omega}$ are the intensities of incident and scattered second-harmonic radiation. K indicates the number of scattered photons captured, which depends on experimental geometry, and thus is approximately constant for a given experimental condition. The first term in equation (1), $K(N_s<\beta_s^2>I_\omega^2$, is the second-harmonic scattering from the solvent, i.e., $I_{2\omega}$(solvent)=$K(N_s<\beta_s^2>I_\omega^2$. Dividing both sides of equation (1) by the latter results in the following equation (2).

$$I_{2\omega}(\text{solution})/I_{2\omega}(\text{solvent})=1+N_c<\beta_c^2>/N_s<\beta_s^2> \quad (2)$$

Equation (2) indicates that the plot of $I_{2\omega}$ (solution)/$I_{2\omega}$ (solvent) according to the chromophore concentration should be a straight line and that the slope and intercept will be $N_c<\beta_c^2>/N_s<\beta_s^2>$ and unity, respectively. The fi values of the chromophores, $\beta_c$, can be calculated from equation (3).

$$\beta_c=(<\beta_c^2>)^{1/2}=(\text{slope}\times N_s<\beta_s^2>)^{1/2} \quad (3)$$

FIG. 1 shows the plots of $I_{2\omega}$ (solution)/$I_{2\omega}$ (solvent) according to the concentration of 1,3,5-tricyano-2,4,6-tris(p-piperidylstyryl)benzene (2i). In all cases, the plots are linear and the intercepts are unity, as expected in equation (3). The results are summarized in Table 1.

The thermal stability of the compounds 1-3 were assessed by measuring the initial decomposition temperatures ($T_d^i$), where the first slope change occurs in the TGA thermogram. The results are summarized in Table 1.

Example 4

Nonlinear Optical Property of 1,3,5-tricyano-2,4,6-tris(vinyl)benzene derivatives in the Powder State The powdered samples were prepared by simply evaporating the solvent from the product solution during the work-up. The XRD data of these samples are the same as those of single crystals and all molecules of the samples are almost in the state of arrangement in the same direction. The intensity of the second harmonic radiation of the powdered samples of compounds 1-3 were measured by the second harmonic with evanescent wave (SHEW) method [*J. Appl. Phys.* 1994, 75, 4332]. The powder samples were packed into a sample holder and pushed in contact with the hemi cylindrical prism of SF59 glass ($n_{780}$=1.8955, $n_{1560}$=1.9253). The incident-angle-dependent second harmonic was detected at the same excitation wavelength used in the HRS measurement. The reliability of this method was confirmed by measuring the d coefficients of the powder sample of m-nitroaniline (mNA). As a result, the intensity of the second harmonic radiation of the powder samples 2g, 2j, and 3j were 3.4, 0.36 and 2.1 times of that of m-nitroaniline, respectively. The results are summarized in Table 1.

Example 5

Two Photon Absorption Cross Sections of 1,3,5-tricyano-2,4,6-tris(vinyl)benzene derivatives The two-photon absorption cross-section of the compounds 1-3 were measured with the two-photon-induced fluorescence method by using the nano-second laser pulses as reported in the literature. An OPO laser (Continuum Surelite OPO, 5 ns pulses), pumped by a Q-switched Nd:YAG laser (Continuum SL-II-10), has been used as the excitation source (pulse duration≈5 ns, repetition rate=10 Hz) [*J. Am. Chem. Soc.* 2000, 122, 9500].

Samples were dissolved in $CHCl_3$ at concentrations of (0.050–1.0)×10⁻⁴ M and the two-photon induced fluorescence intensity was measured according to the concentration. The plot of the fluorescence intensity according to the concentration of samples was a straight line at low concentration but showed a downward curve at higher concentration, due to the formation of the aggregates. Accordingly, the highest concentration determined from the linear region was used to measure the TPA cross section. The TPA cross sections were measured at 780~880 nm using either coumarine 307 in methanol ($1.00\times10^{-4}$ M) or Rhodamine B in methanol ($1.00\times10^4$ M) as a reference [*J. Opt. Soc. Am. B* 1996, 13, 481]. The TPA cross sections were calculated by using equation (4), where the subscripts s and r stand for the sample and reference molecules.

$$\delta = \frac{S_s \Phi_r \phi_r c_r}{S_r \Phi_s \phi_s c_s} \delta_r, \quad (4)$$

Figure 2:
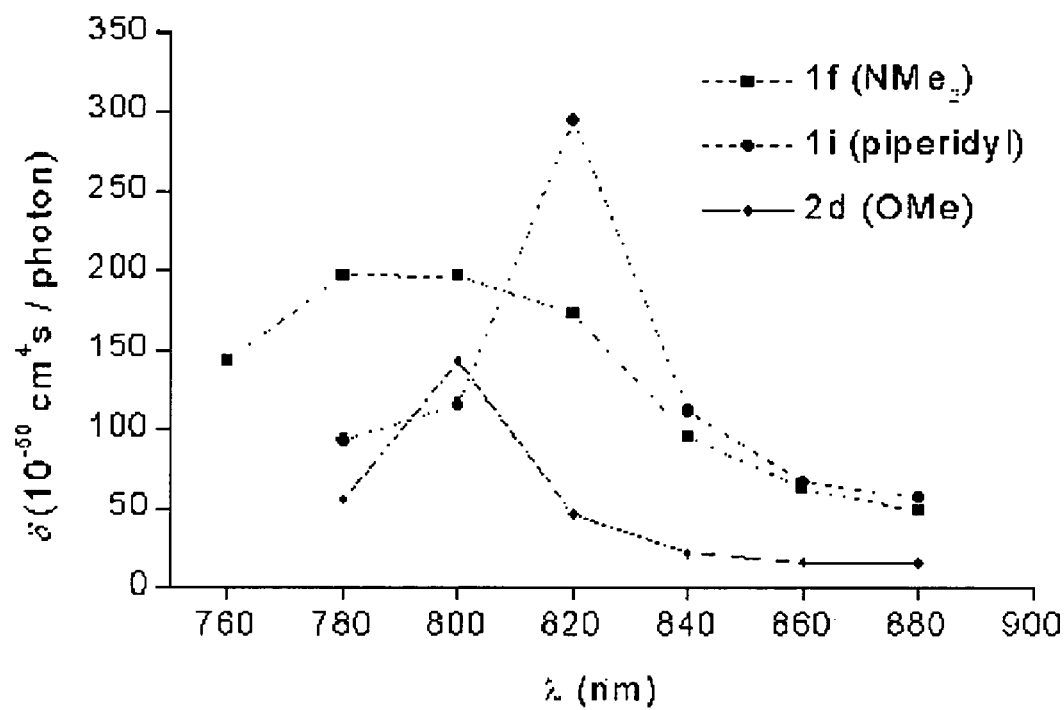
FIG. 2 is a graph showing the two-photon absorption efficiency according to the wavelength of 1,3,5-tricyano-2,4,6-tris(vinyl)benzene derivatives(1f, 1i, 2d), the preferred embodiment of the present invention.
Figure 3:
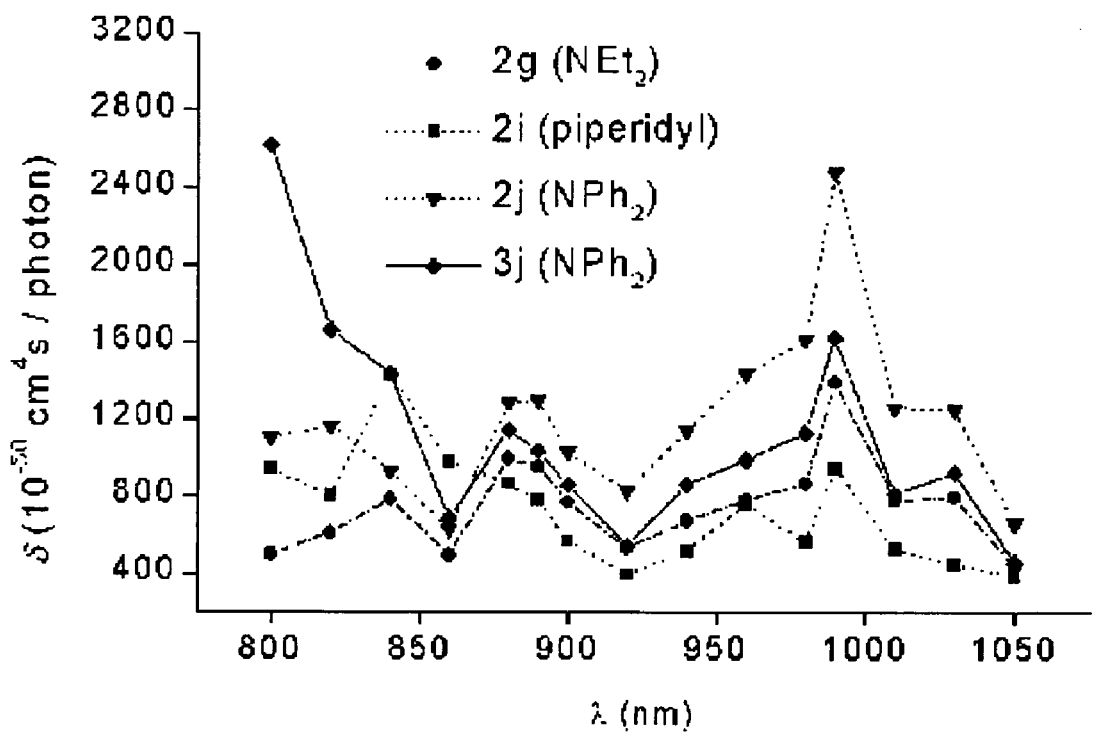
FIG. 3 is a graph showing the two-photon absorption efficiency according to the wavelength of 1,3,5-tricyano-2,4,6-tris(vinyl)benzene derivatives(2g, 2i, 2j, 3j), the preferred embodiment of the present invention.

In the above equation (4), the intensity of the signal collected by a PMT detector was denoted as S. $\Phi$ is the fluorescence quantum yield. $\phi$ is the overall fluorescence collection efficiency of the experimental apparatus. The number density of the molecules in solution was denoted as c. $\delta_r$ is the TPA cross section of the reference molecule. The two-photon-induced fluorescence excitation spectra for compounds 1-3 are shown in FIG. 2 and 3. The wavelengths of the two-photon absorption maxima ($\lambda_{max}^{(2)}$) and the maximum values of the two-photon absorption cross section ($\delta_{max}$) are summarized in Table 1.

As indicated in the below Table 1, 1,3,5-tricyano-2,4,6-tris(vinyl)benzene derivatives 1~3, octupolar molecules, represented by the above formulas 1 and 2 have the second-order nonlinear optical property[$\beta(0)$] of $(14\text{-}124)\times10^{-30}$ esu, and it is shown that the intensity of the second-order harmonic radiation[$\chi^{(2)}$] of the derivatives is about 0.4~3.4 times of that of m-nitroaniline, due to being arranged spontaneously in the solid state. The derivatives are useful in frequency modulation, electro-optic devices, which make a modulation and a switching of the optical signal. They are also useful in extremely-highly integrated optical memory storage, two-photon spectrofluorimeter, 15 two-photon imaging, and two-photon optical power limiting, because the two-photon absorption cross sections ($\delta_{max}$) are (143-2620)×10⁻⁵⁰ cm⁴s/photon.

TABLE 1

| Compd | D | $\lambda^{(1)}_{max}$ | $\beta$ ($10^{-30}$ esu) | $\beta$ ($10^{-30}$ esu) | SHG | $\delta_{max}$ ($\lambda^{(2)}_{max}$) | $T_d^i$/° C. |
|---|---|---|---|---|---|---|---|
| 1f | NMe₂ | 389 | 35 | 25 | | 197(800) | 340 |
| 1h | piperidyl | 396 | 25 | 17 | | 295(820) | 319 |
| 2d | OMe | 388 | 20 | 14 | | 143(800) | 385 |
| 2g | NEt₂ | 493 | 121 | 65 | 3.4 | 1390(990) | 390 |
| 2i | piperidyl | 468 | 118 | 69 | | 1430(840) | 418 |
| 2j | NPh₂ | 488 | 223 | 124 | 0.36 | 2480(990) | 422 |
| 2h | NBu₂ | 499 | 219 | 116 | | | 340 |

TABLE 1-continued

| Compd | D | $\lambda^{(1)}_{max}$ | $\beta$ ($10^{-30}$ esu) | $\beta$ ($10^{-30}$ esu) | SHG | $\delta_{max}$ ($\lambda^{(2)}_{max}$) | $T_d^i/°$ C. |
|---|---|---|---|---|---|---|---|
| 2i | piperidyl | 461 | 178 | 108 | | | 402 |
| 3j | NPh$_2$ | 468 | 184 | 107 | 2.1 | 2620(800) | 404 |

In the above Table 1, $\lambda^{(1)}_{max}$ is the maximum peak in the one-photon absorption spectra in nm and $\beta$ and $\beta(0)$ is the first hyperpolarizability and the corrected values of the first hyperpolarizability at $\lambda \rightarrow \infty$ by using a three-level model. SHG is defined as $N/N_{mNA}$, N and $N_{mNA}$ are the relative values of the intensity of the second-order harmonic radiation generated in the compound 2 and m-nitroainiline, respectively. $\delta_{max}$ indicates the TPA cross sections in the unit of $10^{-50}$ cm$^4$s/photon and $\lambda^{(2)}_{max}$ is the maximum peak in the two-photon absorption spectra in nm. $T_d^i$ is the initial decomposition temperature determined by thermal gravimetric analysis (TGA).

INDUSTRIAL APPLICABILITY

As described in the above, 1,3,5-tricyano-2,4,6-tris(vinyl) benzene derivatives of the present invention have a large first hyperpolarizability and two-photon absorption cross sections in the liquid state, are arranged in the same direction spontaneously in the solid state due to its geometrically structural property and generate a large intensity of the second-order harmonic radiation. The second-order nonlinear optical property is applicable in the treatment of the optical signal such as electro-optic modulator, optical switch and so on in the field of the optical communication. The two-photon absorption property is useful in three-dimensional optical storage, two-photon fluorescence excitation microscopy, two-photon optical power limiting, two-photon upconverted lasing, photodynamic therapy and so on.

What is claimed is:

1. A 1,3,5-tricyano-2,4,6-tris(vinyl)benzene derivative of the formula II:

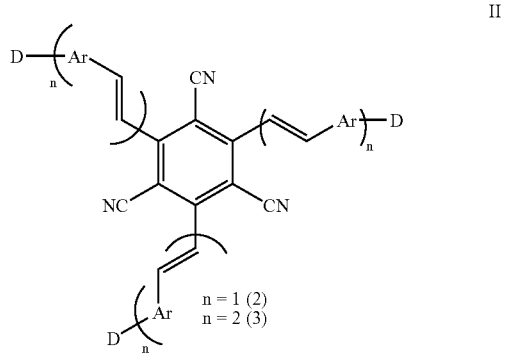

wherein, D is $NR_1R_2$ or $X_1R_3$;
wherein $R_1$, $R_2$ and $R_3$ are independently hydrogen, alkyl, hydroxyalkyl, alkyl moiety, phenyl or aryl moiety, and $X_1$ is oxygen or sulfur; and
Ar is an aromatic group represented by the following chemical formula III and n is 1;

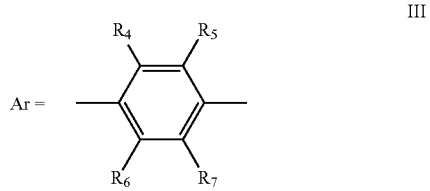

wherein, $R_4$, $R_5$, $R_6$, and $R_7$, are independently hydrogen, halogen, aryl, hydroxy, alkoxy, aryloxy, alkyl, CN, alkyl moiety, phenyl or aryl moiety.

2. A method for preparing 1,3,5-tricyano-2,4,6-tris(vinyl) benzene derivatives, of claim 1, wherein the derivatives are synthesized either by refluxing 1,3,5-tricyanomesitylene with N-formylamine dimethylacetal or substituted benzaldehyde, or by the Wittig reaction of 1,3,5-tricyano-2,4,6-tris[(diethylphosphoryl)methyl]benzene with substituted benzaldehyde.

* * * * *